US006670523B1

(12) United States Patent
Mähr et al.

(10) Patent No.: US 6,670,523 B1
(45) Date of Patent: Dec. 30, 2003

(54) TAMPON WITH INFECTION-PROTECTION

(75) Inventors: Rodolfo Mähr, Schaffhausen (CH);
Andreas Mähr, Schaffhausen (CH);
Heidi Enderli, Zürich (CH)

(73) Assignee: IVF Hartmann AG, Neuhausen von Rheinfall (CH)

( * ) Notice: Subject to any disclaimer, the term of this patent is extended or adjusted under 35 U.S.C. 154(b) by 0 days.

(21) Appl. No.: 09/868,774

(22) PCT Filed: Dec. 20, 1999

(86) PCT No.: PCT/IB99/02025
§ 371 (c)(1),
(2), (4) Date: Sep. 17, 2001

(87) PCT Pub. No.: WO00/37118
PCT Pub. Date: Jun. 29, 2000

(30) Foreign Application Priority Data

Dec. 21, 1998 (CH) .............................................. 2524/98

(51) Int. Cl.$^7$ ................................................. A61F 13/15
(52) U.S. Cl. ...................................... 604/381; 604/904
(58) Field of Search ..................... 604/385.17, 385.18, 604/904, 363, 381

(56) References Cited

U.S. PATENT DOCUMENTS

| 3,693,622 | A | * | 9/1972 | Jones, Sr. ..................... 604/375 |
| 3,902,493 | A | | 9/1975 | Baier et al. ................... 128/270 |
| 3,999,549 | A | * | 12/1976 | Poncy et al. ................... 604/15 |
| 4,309,997 | A | * | 1/1982 | Donald .......................... 604/11 |
| 4,374,522 | A | * | 2/1983 | Olevsky ........................ 604/374 |
| 4,582,717 | A | * | 4/1986 | von Bittera et al. .......... 424/431 |
| 4,952,211 | A | * | 8/1990 | Snider .......................... 604/285 |
| 5,009,890 | A | | 4/1991 | DiPippo ....................... 424/195.1 |
| 5,330,756 | A | * | 7/1994 | Steuart et al. ................ 424/401 |
| 5,607,754 | A | | 3/1997 | Giles et al. ................... 428/211 |
| 5,641,503 | A | | 6/1997 | Brown-Skrobot ........... 424/431 |
| 6,228,373 | B1 | * | 5/2001 | Bergstrand et al. ....... 424/278.1 |

FOREIGN PATENT DOCUMENTS

| AT | 000 654 U1 | 2/1996 |
| DE | PS 19 25 086 | 5/1969 |
| DE | OS 1 541 275 | 11/1969 |
| DE | OS 20 24 930 | 5/1970 |
| EP | 0 599 307 A1 | 6/1994 |

OTHER PUBLICATIONS

Altman, P.M., "Australian Tea Tree Oil–A Natural Antiseptic," *Aufbereitungs Technik, Australian Journal of Biotechnology*, 3(4):247–248 (Oct., 1989).

* cited by examiner

*Primary Examiner*—Weilun Lo
*Assistant Examiner*—C. Lynne Anderson
(74) *Attorney, Agent, or Firm*—Marshall, Gerstein & Borun LLP

(57) ABSTRACT

Disclosed is a tampon that is impregnated with a means which is water-repellent as well as infection inhibitory. Said tampon is thus particularly useful for swimming and bathing. Washing-out of the infection inhibitory component is prevented by using an impregnation means combined of a half-solid or solid support with an infection inhibitory means based on plant oils which act accordingly. The inventive tampon is thus useful for long-term application in water.

15 Claims, No Drawings

TAMPON WITH INFECTION-PROTECTION

CROSS REFERENCE TO RELATED APPLICATIONS

This application claims the priority of Swiss patent application No. 2524/98, filed Dec. 21, 1998, the disclosure of which is enclosed herein in its entirety by reference.

1. Technical Field

The present invention concerns a tampon that is in particular suitable for being used in water, i.e. for bathing or swimming, and that reduces or even fully eliminates the thereby existing danger of infection.

2. Background Art

The imbuing and impregnating of tampons with liquid paraffins and other substances in order to improve the slippage of the tampon and therewith to improve its applicability or to prevent the penetration of water into the vagina upon bathing are known (see e.g. AT 000 654 U1).

From DE-PS 19 25 086, DE-OS 20 24 930 and DE-OS 15 41 275 it is also already known to imbue tampons with e.g. mineral oil as carrier of a drug, or with an aqueous biological therapeutical solution, in order to introduce the pharmaceutical in the exactly desired amount and concentration into the interior of the vagina. U.S. Pat. No. 5,641,503 discloses a tampon comprising a fatty acid ester preventing the toxin production by staphylococcus aureus.

In U.S. Pat. No. 3,902,493 a tampon is described comprising a foam corpus and an overwrap. The overwrap can be impregnated with a therapeucically active agent and a binding lubricant.

It is also already known that the penetration of water into the vagina can cause infections. The goal of the present invention therefore was to not only reduce the penetration of water but to simultaneously prevent or at least significantly reduce the generation of sources of infection by the never completely avoidable contact with water.

DISCLOSURE OF THE INVENTION

This goal was achieved by providing a specific tampon furnished with an impregnating agent and an absorbent tampon body and a holding means for the removal of the tampon from the vagina extending from the tampon body at one side, characterized in that the impregnating agent comprises a physiologically harmless hydrophobic carrier and an essentially also hydrophobic and physiologically harmless desinfectant. The hydrophobic desinfectant consists of substances with infection preventing or at least infection reducing effect. Said substances preferably exhibit antimicrobial and/or antibacterial and/or mycostatic and/or bacteriostatic effect.

The hydrophobic desinfectant preferably comprises a plant oil with the one or more respective effects or a mixture of such plant oils. It is particularly preferred that the desinfectant consists of a plant oil or a mixture of plant oils.

The term "plant oils" as it is used herein always refers to plant oils with desinfecting features, in particular antimicrobial and/or antibacterial and/or mycostatic and/or bacteriostatic effect.

Plant oils are preferred since in general they are relatively non-toxic and well compatible, and since due to their oily, i.e. hydrophobic nature, they are not washed out or only to a small amount. Thereby their remaining in the vaginal region also during a longer stay in the water is guaranteed and their delivery to the environment is minimized. Furthermore, respectively treated tampons can be disposed off without any problem.

In principle the desinfectant can, besides of the plant oil, also comprise further effective substances, in particular for an application aimed at a specific pathogen. Such additive, however, in general should be avoided since a lot of such additives are washed out which affects their effect and may lead to a non-desired environmental pollution.

MODES FOR CARRYING OUT THE INVENTION

The impregnating agent used in the inventive tampon, as desinfectant preferably comprises a plant oil or a mixture of plant oils.

Plant oils or mixtures of plant oils with desinfecting features are known.

Presently preferred plant oils are tee tree oil and hypericon oil (also known as St. John's wort oil) or a combination of both. Said oils exhibit antimicrobial as well as antibacterial, mycostatic and bacteriostatic effect. Furthermore, it has been found that said oils also during longer stay in water are almost not washed out.

The inventive tampon usually comprises an impregnating agent with a carrier that is half-solid or solid. Said criterion on the one hand facilitates the handling since the hands remain proper, on the other hand such carriers are very well suitable for fixing the oil used as desinfectant. The carrier preferably has a melting point of about 38° C. to about 65° C. Particularly suitable as such a carrier is a paraffin or a mixture of paraffins, in particular white petrolatum (vaseline) with a melting point of about 38–60° C., a boiling point of over 300° C. and a density of 0.820–0.880.

Usually, the impregnating agent comprises the desinfectant in an amount of 1 to 10% by weight referred to the weight of the carrier. For the impregnating agent comprising hypericon oil as desinfectant, an amount of at least about 2% by weight, usually about 5% by weight of the hypericon oil is preferred, for a desinfectant comprising the tee tree oil, an amount of at least about 4% by weight, usually 4 to 5% by weight of tee tree oil is preferred, both referred to the weight of the carrier, in particular vaseline.

Although an inventive tampon in principle can be used as protection during taking a bath it is preferred that it is simultaneously applicable during menstrual period. For this purpose it has not only to prevent penetration of water into the vagina but also to simultaneously absorb blood. This combination of requirements is met by a tampon that is only partially impregnated and this such that during use it has a completely impregnated surface on the water side, that is, in the case of a usual tampon embodiment, on the side of the exit of the holding-means-for-its-removal from the absorbing tampon body, while the part opposite to the exit of the holding means, however, is at least partially free of impregnating agent. This can be achieved by several ways, e.g. by only partial immersion into the impregnating agent, by protecting several parts, e.g. by immersion or spraying in a kind of sieve holder etc. A very simple method consists in that the tampon is immersed in the impregnating agent with the side of the exit of the holding means, usually a cord, ahead. By this immersion method furthermore at least the part of the holding means that is adjacent to the absorbing body is impregnated, which proved to be positive for the infection reducing effect.

The not impregnated part preferably is between 10 and 20%, in particular between 12–15% of the tampon surface.

A tampon body can be designed in one part form or in several parts form. For a good protection during taking a bath it is essential that the tampon body as a whole is at least on the side of the holding means provided with impregnating agent, since in the case of an impregnation of e.g. only an overwrap that is wrapped round the "core" afterwards, the overwrap can not be tightly sealed around the holding means such that at least in the region of the holding means water can penetrate the tampon and therewith reduce its absorbing effect as well as the protection against infection. A preferred embodiment of the tampon of the invention comprises the as such at least on the side of the holding means impregnated tampon body and the optionally also at least partially impregnated holding means.

A simple method for the production of a tampon of the invention is characterized in that the impregnating agent is heated to a temperature that is at least 10° C. above the melting point of the carrier, that the tampon is at least partially immersed into the impregnating agent, and that afterwards superfluous impregnating agent is removed from the tampon by allowing said agent to drop off, and cooling to room temperature. A preferred temperature for the application of an impregnating agent with the preferred white vaseline as carrier is about 90° C.–92° C. In consideration of the plant oils higher temperatures should be avoided. The impregnating agent can either be previously mixed or directly prior to the impregnation step. The only fact that matters is that at the time of the impregnation step it is homogeneously mixed. A too long holding of the impregnating agent at high temperature should be avoided. At the temperature of the impregnating agent of about 92° C., an immersion time of 1 to 2 minutes proved to be suitable. After the immersion, a dropping off phase of preferably at least about 20 second is provided, whereafter the tampon is cooled to room temperature. Said cooling can either be made by environmental air or—speeded up—e.g. by application of cool air.

While in the present application preferred embodiments of the invention are described it has to be clearly pointed to the fact that the invention is not restricted to said embodiments and can also be embodied in other way within the scope of the appendant claims.

What is claimed is:

1. A tampon comprising an absorbent tampon body having a first end intended during use to be disposed distal to the opening of the vagina and a second end, intended during use to be disposed proximal to the opening of the vagina; and a holding means, the holding means extending from the second end of the tampon for removal of said tampon from the vagina, wherein the absorbent tampon body is at least partially impregnated with an impregnating agent comprising a physiologically harmless hydrophobic carrier and an essentially hydrophobic and physiologically harmless disinfectant wherein the second end comprising at least 80% of the tampon is completely impregnated with said impregnating agent such that the second end is impermeable to water, and wherein a part of the first end of the tampon, which corresponds to less than 20% of the whole tampon surface, is not completely impregnated and is permeable to water.

2. Tampon according to claim 1, wherein the hydrophobic disinfectant exhibits at least one of the following effects:

antimicrobial effect, antibacterial effect, mycostatic effect, and bacteriostatic effect.

3. Tampon according to claim 1, wherein the hydrophobic disinfectant contains a plant oil or a mixture of plant oils.

4. Tampon according to claim 3, wherein the hydrophobic disinfectant consists of a plant oil or a mixture of plant oils.

5. Tampon according to claim 3, wherein the plant oil is tee tree oil and/or hypericon oil.

6. Tampon according to claim 1, wherein the carrier is semi-solid or solid.

7. Tampon according to claim 6, wherein the carrier has a melting point of about 38° C. to about 65° C.

8. Tampon according to claim 1, wherein the carrier is a paraffin or a mixture of paraffins.

9. Tampon according to claim 1, wherein the impregnating agent comprises said hydrophobic disinfectant in an amount 1 to 10% by weight referred to the weight of the carrier.

10. Tampon according to claim 1, wherein said hydrophobic disinfectant comprised in said impregnating agent is either hypericon oil in amount of about 2% by weight or tee tree oil in an amount of about 4% by weight referred to the weight of the carrier.

11. Tampon according to claim 1, wherein said hydrophobic disinfectant comprised in said impregnating agent is either selected from a group consisting of hypericon oil, tee tree oil, or a combination of both in an amount of about 5% weight referred to the weight of the carrier.

12. Tampon according to claim 1, wherein the tampon is only partially impregnated, wherein the second end has a completely impregnated surface while the first end of the tampon body has a surface that is at least partially free of impregnating agent.

13. Tampon according to claim 12, wherein a part of the first end of the tampon, which corresponds to between 10 and 20% of the whole tampon surface, is not impregnated.

14. Tampon according to claim 12, wherein a part of the first end of the tampon, which corresponds to between 10 and 15% of the whole tampon surface, is not impregnated.

15. Tampon according to claim 8, wherein the paraffin is white petroleum.

* * * * *